(12) United States Patent
Getty et al.

(10) Patent No.: US 8,809,577 B2
(45) Date of Patent: Aug. 19, 2014

(54) PROCESS TO PRODUCE FLUORINATED BETAINES

(75) Inventors: Stephen James Getty, Wilmington, DE (US); Peter Michael Murphy, Chadds Ford, PA (US); Romain Severac, Garginville (FR); Alexander Borisovich Shtarov, Wilmington, DE (US); Hollis Thomas Warren, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 250 days.

(21) Appl. No.: 13/554,659

(22) Filed: Jul. 20, 2012

(65) Prior Publication Data

US 2014/0024855 A1    Jan. 23, 2014

(51) Int. Cl.
*C07C 303/40* (2006.01)

(52) U.S. Cl.
CPC .................................... *C07C 303/40* (2013.01)
USPC ............................... 562/107; 564/96; 564/98

(58) Field of Classification Search
CPC ...................................................... C07C 303/40
USPC ........................................................... 562/107
See application file for complete search history.

(56) References Cited

U.S. PATENT DOCUMENTS

| | | | |
|---|---|---|---|
| 3,721,706 | A | 3/1973 | Stach et al. |
| 4,383,929 | A | 5/1983 | Bertocchio et al. |
| 4,486,391 | A | 12/1984 | Hashimoto |

FOREIGN PATENT DOCUMENTS

| | | | |
|---|---|---|---|
| CN | 102140338 A | | 8/2011 |
| FR | 2453145 A | | 10/1980 |
| JP | 58179300 A | * | 10/1983 |
| JP | 58203959 A | | 11/1983 |
| JP | 59048457 A | | 3/1984 |

OTHER PUBLICATIONS

International Search Report, PCT/US2013/050465, mailed date Oct. 4, 2013.

Kimura, et al, Akita University, Akita, Japan "Preparation and surface active properties of perfluorooctanesulfonamide derivatives" 1982, 448-51. (Abstract).

* cited by examiner

*Primary Examiner* — Yong Chu

(57) ABSTRACT

A process to prepare fluorinated sulfobetaine compounds of formula (I)

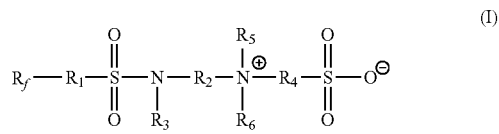

wherein $R_f$ is $C_2$ to $C_{10}$ fluoroalkyl optionally interrupted by one or more of O, $CH_2$, CHF, or combinations thereof; $R_1$ is $C_1$ to $C_{10}$ alkylene; $R_2$ is $C_1$ to $C_6$ alkylene or a chemical bond; $R_3$ is H or $CH_3$; $R_4$ is $C_1$ to $C_6$ alkylene containing at least one hydroxyl group; $R_5$ is H or $CH_3$; and $R_6$ is H or $CH_3$; comprising contacting a fluorinated sulfonamide amine of formula (II)

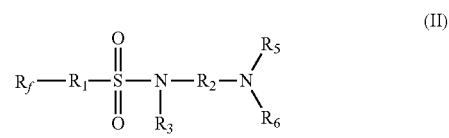

with an aliphatic chlorosulfonic acid or salt thereof of formula (III)

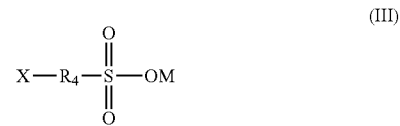

in the presence of water and at least one alkylene glycol, and optionally at least one alkyl carbonate, said fluorinated sulfobetaine having reduced free chloride content and reduced flammability without the need for additional purification steps.

13 Claims, No Drawings

PROCESS TO PRODUCE FLUORINATED BETAINES

FIELD OF THE INVENTION

This invention relates to a process to produce fluorinated betaines having reduced free chloride and low flammability, for use as an active ingredient in fire fighting compositions.

BACKGROUND OF THE INVENTION

Fluorosurfactants which incorporate betaine groups are known for use as additives in fire extinguishing compositions. The betaine group allows such fluorosurfactants to undergo electrostatic interactions with other components in a fire fighting composition therefore improving performance.

In U.S. Pat. No. 4,383,929, Bertocchio et al. disclose fluorinated sulfobetaine compounds and methods for their production. These fluorinated sulfobetaines are prepared by alkylation of a fluorianted amine with either a) sultone propane in chloroform or b) a chlorosulfonic salt in water or ethanol. The aqueous processes disclosed in Bertocchio et al. typically have high chloride contents from around 8 to 16 weight percent. To reduce the chloride content, Bertocchio et al. teach dissolving the dried fluorinated sulfobetaines in highly flammable absolute ethanol, where the metal chloride salts can then be filtered out, distilling the ethanol, and redissolving the solid fluorinated sulfobetaine in water.

The known aqueous processes to produce fluorinated sulfobetaines produce a final product that is high in free chloride. High chloride presents a problem in promoting corrosion in metal storage containers. Current attempts to reduce chloride levels are focused around removal of ethanol and water by distillation to obtain dry fluorinated sulfobetaine, redissolving it in absolute ethanol, filtration of the metal chlorides, followed by distillation of the ethanol and isolation of solid sulfobetaine. While these additional steps reduce the final chloride levels, they are tedious and require large amounts of ethanol, a filtration apparatus, a distillation, and handling powdery or solid products.

Alternatively, to reduce the chloride content, fluorinated sulfobetaines are prepared in flammable organic solvents. The resulting compositions are highly flammable and require removal of flammable organic solvents by distillations to increase the flash point prior to transportation.

A process that results in reduced chlorides without the need to add highly flammable ethanol followed by a distillation of ethanol would not only reduce the cost of production, but also reduce ethanol usage is needed. A process that also results in a stable homogeneous solution of product with a high flash point would allow for transporting the fluorinated sulfobetaines prior to when the final fire fighting foam formulation is needed. The present invention meets these needs of providing a process that produces a a solution of low chloride, high flash point fluorinated sulfobetaine product.

SUMMARY OF THE INVENTION

A process to prepare fluorinated sulfobetaine compounds of formula (I)

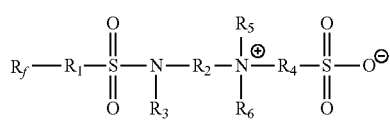

wherein
$R_f$ is $C_2$ to $C_{10}$ fluoroalkyl optionally interrupted by one or more of O, $CH_2$, CHF, or combinations thereof;
$R_1$ is $C_1$ to $C_{10}$ alkylene or a chemical bond;
$R_2$ is $C_1$ to $C_6$ alkylene;
$R_3$ is H or $CH_3$;
$R_4$ is $C_1$ to $C_6$ alkylene containing at least one hydroxyl group;
$R_5$ is H or $CH_3$; and
$R_6$ is H or $CH_3$;
comprising contacting a fluorinated sulfonamide amine of formula (II)

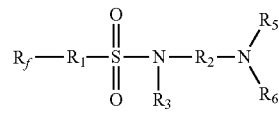

wherein $R_f$, $R_1$, $R_2$, $R_3$, $R_5$ and $R_6$ are each defined as in Formula (I);
with an aliphatic chlorosulfonic acid or salt thereof of formula (III)

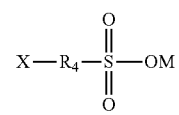

wherein $R_4$ is $C_1$ to $C_6$ alkylene containing at least one hydroxyl group; X is chlorine; and M is Na, K, Li, or Ca;
in the presence of water and at least one alkylene glycol and optionally at least one alkyl carbonate; wherein the ratio of water to the total amount of alkylene glycol and optional alkyl carbonate is from about 1:19 to about 1:3.

DETAILED DESCRIPTION

The present invention relates to a process to prepare fluorinated sulfobetaine compounds of formula (I)

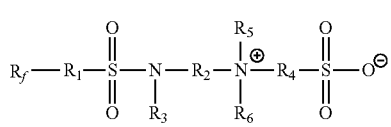

wherein
$R_f$ is $C_2$ to $C_{10}$ fluoroalkyl optionally interrupted by one or more of O, $CH_2$, CHF, or combinations thereof;
$R_1$ is $C_1$ to $C_{10}$ alkylene or a chemical bond;
$R_2$ is $C_1$ to $C_6$ alkylene;
$R_3$ is H or $CH_3$;
$R_4$ is $C_1$ to $C_6$ alkylene containing at least one hydroxyl group;
$R_5$ is H or $CH_3$; and
$R_6$ is H or $CH_3$;
comprising contacting a fluorinated sulfonamide amine of formula (II)

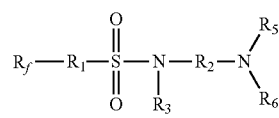

wherein $R_f$, $R_1$, $R_2$, $R_3$, $R_5$ and $R_6$ are each defined as in Formula (I);

with an aliphatic chlorosulfonic acid or salt thereof of formula (III)

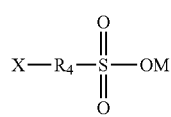

wherein $R_4$ is $C_1$ to $C_6$ alkylene containing at least one hydroxyl group; X is chlorine; and M is Na, K, Li, or Ca; in the presence of water and at least one alkylene glycol and optionally at least one alkyl carbonate; wherein the ratio of water to the total amount of the alkylene glycol and optional alkyl carbonate is from about 1:19 to about 1:3.

Preferred fluorinated sulfobetaine compounds generated by the process of the present invention are those of formula (I) wherein $R_f$ is $C_2$ to $C_6$ fluoroalkyl. More preferred are those wherein $R_f$ is $C_2$ to $C_4$ fluoroalkyl.

In another embodiment preferred fluorinated sulfobetaine compounds generated by the process of the present invention are those of formula (I) wherein $R_1$ is $C_1$ to $C_6$ alkylene. More preferred are those wherein $R_1$ is $C_1$ to $C_4$ alkylene. More preferred are those wherein $R_1$ is $C_2$ alkylene.

Another preferred embodiment is wherein fluorinated sulfobetaine compounds generated by the process of the present invention are those of formula (I) wherein $R_f$ is $C_4$ to $C_6$ fluoroalkyl, and $R_1$ is $C_2$ to $C_4$ alkylene. Also preferred embodiment is wherein $R_f$ is $C_4$ to $C_6$ fluoroalkyl, and $R_1$ is $C_2$ alkylene.

A further preferred embodiment is wherein $R_f$ is $C_2$ to $C_4$ fluoroalkyl, and $R_1$ is $C_2$ to $C_4$ alkylene. Also preferred is wherein $R_f$ is $C_2$ to $C_4$ fluoroalkyl, and $R_1$ is $C_2$ alkylene.

In a further embodiment the contacting of the compounds of formula (II) and formula (III) is conducted in the presence of water, at least one alkylene glycol, and optionally at least one alcohol of low flammability. Additionally the contacting can be conducted in the presence of water, alkylene glycol, alkyl carbonate, and alcohol of low flammability.

The fluoroinated sulfonamide amines of formula (II)

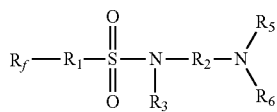

wherein $R_f$, $R_1$, R, $R_3$, $R_4$, $R_5$, and $R_6$ are as defined above, useful in the present invention are commercially available or can be produced by synthesis. To produce fluorinated sulfonamide amines of formula (II), for example, fluorinated alkyl sulfonyl chloride, $R_fR_1SO_2Cl$, wherein $R_f$ and $R_1$ are each defined as above for Formula (II), is reacted with alkyl diamine containing at least one secondary amine, such as 2-(dimethylamino)ethyl](methyl)amine, to produce fluorinated sulfonamide amines of formula (II). Fluorinated alkyl sulfonyl chlorides are prepared by reacting fluorinated alkyl thiocyanates with chlorine. Fluorinated thiocyanates can be prepared from fluorinated iodides according to procedures described in J. Fluorine Chemistry, 42(1), 59-68, (1989). One example is the reaction of the fluoroalkyl ethylene iodides with sodium thioacetate, followed by hydrolysis.

In the process of the present invention, the contacting of the fluorinated sulfonamide amine of formula (II) with the aliphatic chlorosulfonic acid or salt thereof of formula (III) is accomplished in the presence of a solvent comprising water and one or more alkylene glycols. Examples of alkylene glycols include ethylene glycol, propylene glycol, butylene glycol, hexylene glycol, polyethylene glycol, polyethylene glycol alkyl ethers such as butyl diethylene glycol, polypropylene glycol alkyl ethers, ethylene glycol/propylene glycol copolymers, and the like. Preferred in one embodiment is the use of two alkylene glycols. In this embodiment, two glycols, such as hexylene glycol and ethylene glycol are used. The ratio of the water to alkylene glycols is from about 1:19 to about 1:3. A preferred ratio is from about 1:10 to about 1:4. A more preferred ratio is from about 1:7 to about 1:5. The amount of the alkylene glycol and water present relative to the fluorinated sulfonamide amine will vary, provided that amount of the water/alkylene glycol present is suitable for dissolving all of the fluorinated sulfobetaine.

The aliphatic chlorosulfonic acid or salt thereof of formula (III)

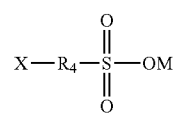

wherein X is Cl, $R_4$ is $C_1$ to $C_6$ alkylene containing at least one hydroxyl group, and M is Na, K, Li, or Ca, which is useful in the process of the present invention is commercially available. For example, $R_4$ can be a divalent radical group or a hydroxy alkylene divalent group. Examples of each are, but not limited to, 2-hydroxypropylene, 1-hydroxypropylene, and 1-hydroxybutylene. Compounds of formula (III) include, but are not limited to, 3-chloro-2-hydroxypropane sulfonic acid sodium salt, 3-chloro-1-hydroxypropane sulfonic acid sodium salt, 4-chloro-1-hydroxybutane sulfonic acid sodium salt, 4-chloro-3-hydroxybutane sulfonic acid sodium salt, and 4-chloro-2-hydroxybutane sulfonic acid sodium salt.

The process of the present invention can occur at temperatures from about 80 to about 120° C., preferably from about 90 to about 110° C. The reaction is allowed to occur for any length of time suitable enough to convert the fluorinated sulfonamide amine to the resulting fluorinated sulfobetaine of formula (I), preferably from about 20 to about 40 hours. Following the reaction, the fluorinated sulfobetaine solution is filtered to remove metal chlorides yielding a reduced chloride content of less than 3% per weight of the fluorinated sulfobetaine.

To further improve the removal of metal chlorides, the fluorinated sulfobetaine solution can be optionally diluted with glycols or alkyl carbonate solvents, and a portion of the water is optionally distilled out prior to filtration. The examples of alkyl carbonate solvents include diethyl carbonate, propylene carbonate, and ethylene carbonate. The optional distillation of a portion of the water is achieved under atmospheric or reduced pressure. However, this optional dilution and distillation step is not required to achieve the low chloride content using the process of the present invention.

The filtrate, comprising the fluorinated sulfobetaine of formula (I), water, alkylene glycol, optionally other co-solvents including alkyl carbonate, and other optional alcohol solvents with low flammability, can then be diluted with water, or with water and other optional co-solvents, to provide a stable solution having a solids concentration of from about 20 weight % solids to about 40 weight % solids relative to the overall amount of the solution. Optional alcohol solvents include, but are not limited to 1-pentanol, 4-methyl-2-pentanol, and 1-hexanol. Preferred alkylene glycol, alkyl carbonate and alcohol solvents are those having a flash point above about 38° C., and more preferably above 69° C. As used herein, the term "low flammability" means having a flashpoint above 38° C., and the term "high flammability" means having a flashpoint below 38° C.

The fluorinated sulfone betaines of formula (I) produced by the present invention have a reduced chloride content compared to fluorinated sulfobetaine produced by alternate prior art methods. Metal chlorides are an unwanted byproduct of the alkylation reaction of the fluorinated amine and the chlorosulfonic acid salt. The process of the present invention produces fluorinated sulfobetaines having less than 3.0% by weight free chloride per weight of fluorinated sulfobetaines. Preferably, the fluorinated sulfobetaines have less than 2% by weight free chloride. More preferably the fluorinated sulfobetaines have less than 1.5% by weight free chloride. Known procedures for producing fluorinated sulfobetaines are typically in water and can contain ethanol. Chloride content is above 3 weight %, and can be as high as 6 weight %.

Fluorinated sulfobetaines produced by the process of the present invention have a flash point above 60° C. and most preferably above 93° C. The fluorinated sulfobetaines are stable in aqueous solution, or in a solution of water and other co-solvents having low flammability. Aqueous solutions of fluorinated sulfobetaines made by the prior art processes tend to separate into two phases at ambient temperature. Those made by the process of the present invention yield homogenous aqueous solutions that are stable over time and can be shipped and stored.

The fluorinated sulfobetaines prepared according to the process of the present invention lower the surface tension of aqueous solutions and are useful foaming agents and therefore are useful as additives in multipurpose fire fighting foam concentrates. In particular, the firefighting foam concentrates are intended for combating hydrocarbon fires, such as fires in which the hydrocarbons are petrols, oils, diesel oil, fuel oil, heptane, hexane or cyclohexane; or for combatting polar liquid fires, such as fires in which the polar liquids are alcohols (for example, methanol, ethanol and isopropanol), ketones (for example, dimethyl ketone and methyl isobutyl ketone), esters (for example, n-butyl acetate) and ethers (for example, methyl tert-butyl ether). The fluorobetaine compounds are also useful as additives in multipurpose fire fighting foam concentrates or compositions intended for combating Class A fires which are fires fueled by burning materials which leave an ash residue such as paper, wood, cloth, rubber, and certain plastics. The fluorinated sulfobetaines produced by the process of the present invention have low chloride content, low flammability, high flash point, and are stable in solution without the need for additional purification steps as required by other prior art processes.

Materials and Test Methods

The following materials and test methods were used in the examples herein.

Materials

N-[3-(Dimethylamino)propyl]-8,8,8,7,7,6,6,5,5,4,4,3,3-tridecafluorooctanesulfonamide was obtained from E. I. du Pont de Nemours and Company, Wilmington, Del.

Other reagents were commercially available from Aldrich Chemical Co., Milwaukee, Wis.

Test Method 1—Surface Tension Measurement

Surface tension was measured using a Kruss Tensiometer, K11 MK2 Version 2.903 in accordance with instructions with the equipment. The Wilhelmy Plate method was used. A vertical plate of known perimeter was attached to a balance, and the force due to wetting was measured.

Test Method 2—Fire Extinguishing Time

Extinguishing times were measured according to the following procedure. 150 mL of acetone was poured into a circular metal container with an internal diameter of 115 mm. Moreover, an aqueous solution composed of the fire fighting foam concentrate diluted to 6 percent by weight in tap water was prepared. This solution was the foaming solution. A rotary stirrer composed of a motor and a metal rod, at the end of which were attached paddles produced a mechanical effect when the rod was being rotated; the rotational speed is adjustable from 1 to 2,800 rpm. The rod was introduced into the bottom and with an outlet orifice located at the top. A metering pump transfered, via the inlet orifice, the aqueous solution to the bottom of the cylindrical container; foam was produced on contact with the rotating paddles, which foam was discharged as it was formed, via the outlet orifice. The throughput of the pump and the rotational speed of the rod ware adjusted so that foam was continuously produced with a stationary foam throughput equal to about 40 g per minute. When the foam throughput was stabilized, the acetone was ignited. After the acetone burned for 90 seconds, the foam was poured into the metal container via a single point situated on the circumference. When the acetone was completely extinguished, the extinguishing time was recorded. The foam concentrates with the best performance on polar solvent were those for which the extinguishing time was as low as possible.

Test Method 3—Re-Ignition Time

Re-ignition times were measured according to the following procedure. This parameter can be evaluated if the extinguishing time was less than 120 seconds. In this case, the foam was poured over the acetone even after the fire seat was extinguished. In all the cases described here, the foam was poured for 120 seconds. Sixty seconds after the pouring of the foam was halted, the contents of the re-ignition vessels (metal container with a diameter of 55 mm and height of 40 mm filled with acetone to a height of 22 mm) were ignited. The re-ignition vessel was placed at the center of the metal container described above, the surface of fuel present in the said container being kept covered with foam. The time at the end of which the flames destroyed 25% of the surface initially covered by the foam, and spread in a lasting fashion over the surface of the metal container, was recorded. A greater time indicated better ability of the foam to prevent the resurgence of the fire.

Fire Fighting Formulation

For Test Methods 2 and 3, the following formulation was used.

| Component* | Weight | Source |
|---|---|---|
| KELZAN | 5 g | CP Kelco |
| DOWANOL DPM | 100 g | Dow Chemical |
| TEXAPON 842 | 80 g | Cognis |
| TEGOTENS AMVSF | 24 g | Degussa |
| TRITON BG-10 | 17 g | Dow Chemical |
| Test Compound | 50 g of active ingredient | |
| FORAFAC 1268 | 26 g | E. I. du Pont de Nemours and Company |
| Water | Up to 1000 g | |

*Trademark indicated by capitalization.

This solution was diluted at 3% in tap water and applied as a foam at the surface of the burning liquid. The components of the above formulation were commercially available from the company indicated.

EXAMPLES

Example 1

N-[3-(Dimethylamino)propyl]-8,8,8,7,7,6,6,5,5,4,4,3,3-tridecafluorooctanesulfonamide (35.1 g, 0.068 mol), 3-chloro-2-hydroxy-1-propanesulfonic acid sodium salt hydrate (14.4 g), hexylene glycol (27.75 g), ethylene glycol (12.28 g), and deionized water (4.08 g) were added to a three-neck roundbottom flask equipped with stir bar, thermocouple, heating mantle, nitrogen blanket, and condenser and the mixture was heated at 103° C. for 24 hours. The reaction mixture was filtered from the white solids (sodium chloride) and diluted with an additional 56.4 g water to dissolve fluorinated sulfobetaine of formula (I). Percent solids were measured as 28.71% solids. The chloride content was measured to be 0.64% (2.2% per weight of fluorinated sulfobetaine) at pH=8.29. The flash point was measured and was greater than 93° C. The product was added to deioinized water by weight based on solids of the surfactant in the solution and tested for surface tension according to Test Method 1. The standard deviation was measured and was less than 1 mN/m, and the temperature was about 23° C. Normal surface tension of deioinized water is 72 mN/m. Results are in Table 1.

TABLE 1

Surface Tension Measurement

| Concentration, % | Surface Tension, mN/m |
| --- | --- |
| 0.0025 | 36.6 |
| 0.005 | 31.6 |
| 0.01 | 26.2 |
| 0.025 | 22.9 |
| 0.05 | 19.1 |
| 0.1 | 18.7 |

Example 2

N-[3-(Dimethylamino)propyl]-8,8,8,7,7,6,6,5,5,4,4,3,3-tridecafluorooctanesulfonamide (29.00 g, 0.057 mol) was dissolved at 100° C. in hexylene glycol (23.56 g), propylene glycol (18.14 g), and water (3.68 g) in a 250 mL, three-neck roundbottom flask equipped with stir bar, thermocouple, heating mantle, nitrogen blanket, and condenser. 3-chloro-2-hydroxy-1-propanesulfonic acid sodium salt hydrate (11.55 g) was added to the flask, and the mixture heated at 100° C. for 21 hours. The reaction mixture was filtered under vacuum at 100° C., removing a small amount of white solid (sodium chloride) and diluted with an additional water (50.65 g). The final composition, fluorinated sulfobetaine of formula (I) was stirred in order to obtain homogeneous solution. Percent solids were measured as 27.51%. The chloride content was measured to be 0.51% (1.85% per wt. of fluorosurfactant). A fire fighting foam was prepared using the formulation previously described and extinction and re-ignition times were measured using Test Methods 2 and 3. The resulting data are in Table 3.

Example 3

N-[3-(Dimethylamino)propyl]-8,8,8,7,7,6,6,5,5,4,4,3,3-tridecafluorooctanesulfonamide (30 g, 0.059 mol), 3-chloro-2-hydroxy-1-propanesulfonic acid sodium salt hydrate (11.75 g), hexylene glycol (19.8 g), 1,2-butanediol (15.0 g), and deionized water (3.74 g) were added to a three-neck roundbottom flask equipped with stir bar, thermocouple, heating mantle, nitrogen blanket, and condenser, and the mixture heated at 103° C. for 21 hours. The hot reaction mixture was decanted from the white solids (sodium chloride) present and diluted with water. The final composition, fluorinated sulfobetaine of formula (I) was stirred in order to obtain homogeneous solution. Percent solids were measured as 22.6%. The chloride content was measured to be 0.48% (2.1% per weight of fluorinated sulfobetaine).

Example 4

N-[3-(Dimethylamino)propyl]-8,8,8,7,7,6,6,5,5,4,4,3,3-tridecafluorooctanesulfonamide (35 g, 0.068 mol), 3-chloro-2-hydroxy-1-propanesulfonic acid sodium salt hydrate (14.11 g), hexylene glycol (14.35 g), 1,2-propylene glycol (10.33 g), and deionized water (3.57 g) were added to a three-neck roundbottom flask equipped with stir bar, thermocouple, heating mantle, nitrogen blanket, and condenser, and the mixture heated at 103° C. for 21 hours. Additional hexylene glycol (1.75 g), and propylene carbonate (14.0 g) were added, and the reaction mixture was filtered from white solids (sodium chloride), and diluted with an additional 46 g of water. The final composition, fluorinated sulfobetaine of formula (I) was stirred in order to obtain homogeneous solution. Percent solids were measured as 33.23%. The chloride content was measured to be 0.426% (1.3% per weight of fluorinated sulfobetaine). The flash point of the resulting fluorinated betaine solution was above 99° C.

Example 5

N-[3-(Dimethylamino)propyl]-8,8,8,7,7,6,6,5,5,4,4,3,3-tridecafluorooctanesulfonamide (45 g, 0.088 mol), 3-chloro-2-hydroxy-1-propanesulfonic acid sodium salt hydrate (18.15 g), hexylene glycol (22.5 g), 1,2-propylene glycol (14.85 g), and deionized water (10.28 g) were added to a three-neck roundbottom flask equipped with stir bar, thermocouple, heating mantle, nitrogen blanket, and condenser, and the mixture heated at 103° C. for 21 hours. The reaction mixture was heated to 115-130° C. with the flow of nitrogen to remove 8.0 g of water. The hot reaction mixture was filtered at 80-90° C. from white solids (sodium chloride), and diluted with water. The final composition, fluorinated sulfobetaine of formula (I) was stirred in order to dissolve. Percent solids were measured as 43.44%. The chloride content was measured to be 0.45% (1.0% per weight of fluorinated sulfobetaine). The mixture was further diluted with ethylene carbonate and water (ratio 1:1.3) to obtain homogeneous solution containing 29.4% solids.

Example 6

N-[3-(Dimethylamino)propyl]-8,8,8,7,7,6,6,5,5,4,4,3,3-tridecafluorooctanesulfonamide (45.0 g, 0.088 mol), 3-chloro-2-hydroxy-1-propanesulfonic acid sodium salt hydrate (18.15 g), hexylene glycol (14.86 g), 1,2-propylene glycol (14.86 g), and deionized water (4.44 g) were added to a three-neck round bottom flask equipped with stir bar, thermocouple, heating mantle, nitrogen blanket, and condenser, and the mixture heated at 103° C. for 24 hours. The reaction mixture was further diluted with hexylene glycol (13.5 g), 4-methyl-2-pentanol (5.86 g), and filtered at 90° C. from white solids (sodium chloride), and diluted with 42 g of water to obtain homogeneous solution containing fluorinated sulfobetaine of formula (I). Percent solids were measured as 36.5%. The chloride content was measured to be 0.53% (1.5% per weight of fluorinated sulfobetaine). The mixture was further diluted with water, 4-methyl-2-pentanol, hexylene glycol, and 1,2-propylene glycol (ratio 21:6:3:4) to 30% solids. The flash point of the resulting fluorinated betaine solution was 72° C.

Comparative Example A

N-[3-(Dimethylamino)propyl]-8,8,8,7,7,6,6,5,5,4,4,3,3-tridecafluorooctanesulfonamide (378 g, 0.738 mol), 3-chloro-2-hydroxy-1-propanesulfonic acid sodium salt hydrate (153 g), ethanol (347 g), and deionized water (201 g) were added to a three-neck roundbottom flask equipped with a mechanical stirrer, thermocouple, heating mantle, nitrogen blanket, and condenser and the mixture was heated at 82° C. for 24 hours. The reaction mixture was filtered from the white solids (sodium chloride) and diluted with an additional 860 g water to give a solution of the sulfobetaine of formula (I), nominally containing 27.1% solids. The chloride content of this solution was measured to be 1.33% (4.9% per weight of fluorinated sulfobetaine). Flash point of this solution was determined to be 35° C. The product was added to deioinized water by weight based on solids of the surfactant in the solution and tested for surface tension according to Test Method 1. Standard deviation was less than 1 mN/m, and the temperature was about 23° C. The normal surface tension of deioinized water is 72 mN/m. Results are in Table 2. A fire fighting foam was prepared using the formulation as previously described with the test methods. Extinction and re-ignition times were measured according to Test Methods 2 and 3. Results are in Table 3.

TABLE 2

| Surface Tension Measurement | |
| --- | --- |
| Concentration, % | Surface Tension, mN/m |
| 0.06 | 19.8 |

TABLE 3

| Example | Extinction time, seconds | Re-ignition time, minutes |
| --- | --- | --- |
| 2 | 1.30 | 6.30 |
|  | 1.13 | 7.05 |
| A | 1.30 | 5.30 |
|  | 1.35 | 5.30 |

Table 3 provides data demonstrating that fire-fighting foam containing a compound prepared by the process of the present invention (Example 2) had superior re-ignition times versus Comparative Example A prepared using a prior art process.

What is claimed is:

1. A process to prepare fluorinated sulfobetaine compounds of formula (I)

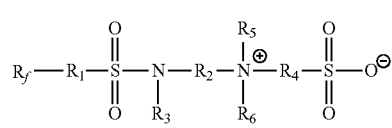

wherein
$R_f$ is $C_2$ to $C_{10}$ fluoroalkyl optionally interrupted by one or more of O, $CH_2$, CHF, or combinations thereof;
$R_1$ is $C_1$ to $C_{10}$ alkylene or a chemical bond;
$R_2$ is $C_1$ to $C_6$ alkylene;
$R_3$ is H or $CH_3$;
$R_4$ is $C_1$ to $C_6$ alkylene containing at least one hydroxyl group;
$R_5$ is H or $CH_3$; and
$R_6$ is H or $CH_3$;
comprising contacting a fluorinated sulfonamide amine of formula (II)

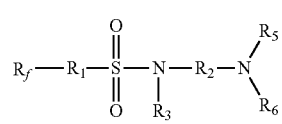

wherein $R_f$, $R_1$, $R_2$, $R_3$, $R_5$ and $R_6$ are each defined as in Formula (I);
with an aliphatic chlorosulfonic acid or salt thereof of formula (III)

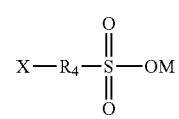

wherein $R_4$ is $C_1$ to $C_6$ alkylene containing at least one hydroxyl group; X is chlorine; and M is Na, K, Li, or Ca; in the presence of water and at least one alkylene glycol, and optionally at least one alkyl carbonate, wherein the ratio of water to the total amount of alkylene glycol and optional alkyl carbonate is from about 1:19 to about 1:3.

2. The process of claim 1 wherein the contacting is conducted in the presence of water, alkylene glycol, alkyl carbonate, and optionally an alcohol of low flammability.

3. A process of claim 1 wherein the contacting occurs at a temperature from about 80° C. to about 120° C.

4. A process of claim 1 wherein the contacting occurs in the presence of water and at least two alkylene glycols.

5. A process of claim 4 wherein the two alkylene glycols are hexylene glycol and 1,2-propylene glycol.

6. A process of claim 1 wherein $R_f$ is $C_4$ to $C_6$ fluoroalkyl and $R_1$ is $C_2$ alkylene.

7. A process of claim 1 wherein the ratio of water to the total amount of alkylene glycol and optional alkyl carbonate is from about 1:10 to about 1:4.

8. A process of claim 1 wherein a solution of the compound of formula (I) is filtered to remove metal chlorides, and after such filtering has a free chloride content of less than 3% by weight of compound of formula (I).

9. A process of claim 8 wherein one or more additional organic solvents chosen from glycols, alkyl carbonates or alcohols are added to the solution of compound of formula (I) prior to filtering.

10. A process of claim 8 wherein the solution of compound of formula (I) is heated to partially distill out water prior to filtering.

11. A process of claim 8 wherein the solution of compound of formula (I), after filtering, is diluted with water and optionally other organic co-solvents to yield a stable solution.

12. A process of claim 9 wherein the solution of compound of formula (I), after filtering, is diluted with water and optionally other organic co-solvents to yield a stable solution.

13. A process of claim 10 wherein the solution of compound of formula (I), after filtering, is diluted with water and optionally other organic co-solvents to yield a stable solution.

* * * * *